US006875885B2

(12) United States Patent
Brown et al.

(10) Patent No.: US 6,875,885 B2
(45) Date of Patent: Apr. 5, 2005

(54) PROCESS FOR THE PREPARATION OF ENANTIOMERICALLY PURE PYRETHROID INSECTICIDES

(75) Inventors: Stephen Martin Brown, Huddersfield (GB); Brian David Gott, Huddersfield (GB)

(73) Assignee: Syngenta Limited (GB)

( * ) Notice: Subject to any disclaimer, the term of this patent is extended or adjusted under 35 U.S.C. 154(b) by 30 days.

(21) Appl. No.: 10/332,884

(22) PCT Filed: Jul. 16, 2001

(86) PCT No.: PCT/GB01/03180

§ 371 (c)(1),
(2), (4) Date: May 6, 2003

(87) PCT Pub. No.: WO02/06202

PCT Pub. Date: Jan. 24, 2002

(65) Prior Publication Data

US 2003/0199709 A1 Oct. 23, 2003

(30) Foreign Application Priority Data

Jul. 18, 2000 (GB) .............................. 0017617

(51) Int. Cl.$^7$ .............................................. C07C 69/74
(52) U.S. Cl. ..................... 560/124; 562/460; 510/302; 252/175
(58) Field of Search .................. 560/124; 562/460, 562/400; 510/302; 252/175

(56) References Cited

U.S. PATENT DOCUMENTS

| | | | | |
|---|---|---|---|---|
| 4,166,064 A | * | 8/1979 | Kondo et al. ............... | 549/499 |
| 4,335,252 A | * | 6/1982 | Engel .......................... | 560/124 |
| 4,429,149 A | * | 1/1984 | Engel .......................... | 560/124 |

* cited by examiner

Primary Examiner—Rita Desai
Assistant Examiner—Hector M. Reyes
(74) Attorney, Agent, or Firm—Thomas Hamilton (57) ABSTRACT

A process for producing compounds of formula (VIIa) and (VIIb) wherein X is a leaving group; Y and $Y^1$ are idependently Cl or Br; and Z is Cl, Br or a haloalkyl group which process comprises a) reacting a compound of formula (VII) wherein X, Y, $Y^1$ and Z are as defined for compounds (VIIa) and (VIIb) with a substantially optically pure chiral amine in a solvent to form a diastereoisomeric salt; b) separating the diastereomeric salt of each enantiomer; c) converting the diastereomeric salt of each anantiomer separately to compounds of formulae (VIIa) and (VIIb) respectively by acid or base hydrolysis, the use of the compounds in making pyrethroid insecticides and novel intermediates.

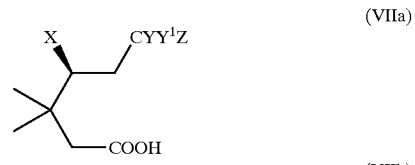

(VIIa)

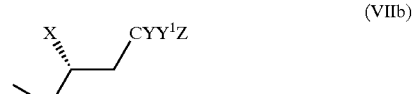

(VIIb)

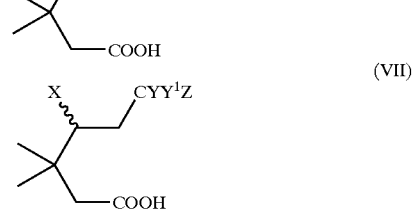

(VII)

13 Claims, 1 Drawing Sheet

Figure 1

X-ray crystal structure of the compound of formula VIIa where X, Y and $Y^1$ are Cl and Z is $CF_3$

PROCESS FOR THE PREPARATION OF ENANTIOMERICALLY PURE PYRETHROID INSECTICIDES

"This application is a 371 of International Application No. PCT/GB01/03180, filed Jul. 16, 2001, the5 contents of which are incorporated herein by reference."

The present invention relates to a process for making cyclopropanecarboxylic acid esters, to intermediates used in the process and their use in making insecticides and acaricides.

Cyclopropanecarboxylic acids are useful in the synthesis of pyrethroid insecticides and acaricides. Particularly important pyrethroid intermediates are compounds of formula (III).

III wherein Y is Cl or Br and Z is Cl, Br or a haloalkyl group.

Compounds of formula (III) may, as discussed below, be converted to certain compounds of formula (I):

I wherein Y is Cl or Br and Z is Cl, Br or a haloalkyl group and E is an insecticidally active ester moiety such as those derived from 4-alkyltetrafluorobenzyl alcohols (especially 4-methyltetrafluorobenzyl alcohol), 4-alkoxytetrafluorobenzyl alcohols, α-cyano-3-phenoxybenzyl alcohol, 3-phenoxybenzyl alcohol and 2-methyl-3-phenylbenzyl alcohol.

It will be appreciated by those skilled in the art that compounds of formula (III) can exist in several stereoisomeric forms. If X and Y are different, there are a total of 3 stereocentres leading to a total of 8 possible stereoisomers. Four of these isomers have the cis stereochemistry about the cyclopropane ring and four of them are trans. Esters of cis-3-(haloalkenyl)-2,2-dimethylcyclopropanecarboxylic acid of formula (III) with for example 4-alkyltetrafluorobenzyl alcohols (especially 4-methyltetrafluorobenzyl alcohol), 4-alkoxytetrafluorobenzyl alcohols, α-cyano-3-phenoxybenzyl alcohol, 3-phenoxybenzyl alcohol and 2-methyl-3-phenylbenzyl alcohol are important insecticidal and acaricidal products, and these acids are important intermediates in the manufacture of such products. When Y and Z are different, each cis form of the compound of the formula (III) is comprised of two geometrical isomers, named Z and E isomers and it is the Z isomer that is desirable when Y=Cl and Z is haloalkyl. Furthermore, when Y and Z are different, each cis-Z form of the compound of the formula (III) is comprised of two enantiomers, sometimes referred to as optical isomers and usually described in terms of the direction in which they rotate plane polarised light, either (+) or (−). Alternative nomenclature is based on the absolute configuration of the Cl position of the cyclopropane ring, either 1R or 1S. The most desirable enantiomers of pyrethroids acids are the cis 1R (+) enantiomers as these have superior insecticidal activity. However, other enantiomers may also be used to make highly active insecticides such as 1R trans S cypermethrin (i.e. Y=Z=Cl) (WO97/14308 and J. Environ. Sci. Health, Part B (1996), B31(3), 527). It is therefore desirable to manufacture certain pyrethroid products as single enantiomers or in enantiomerically enriched form.

The manufacture of single enantiomers or enantiomerically enriched products on an industrial scale is a very complex procedure. One approach to the synthesis of single enantiomer or enantiomerically enriched products is to use intermediates which contain the desired stereochemistry. For example to make the compounds of formula 1' below (containing 3 asymmetric carbon atoms as indicated by an *) the synthesis could use enantiomeric forms or enantiomerically enriched forms of compounds of formula (II), (III), (IV), (V), (VI) or (VII) as shown, wherein X is a leaving group such as Cl or Br; Y and $Y^1$ are independently Cl or Br; Z is Cl, Br or a haloalkyl group and R is H or an alkyl group.

-continued

I'

Enantiomeric forms or enantiomerically enriched forms of compounds (II), (III), (IV), (V), (VI) or (VII) are not available commercially and it is therefore desirable to find a process to resolve one of the above racemic compounds. It is preferable to introduce the resolution of enantiomers as early as possible in the synthetic process (for cost and output reasons). Thus in the process shown in the above scheme the compound of choice for resolving into a single enantiomer would be a compound of formula (VII). However there are no known techniques for the resolution of compounds of formula (VII) or similar compounds because resolution of acids with a chiral centre so remote from the group used to form the diastereoisomeric derivative is unusual if not unknown. One particular difficulty associated with any process for resolving compounds of formula (VII) is the necessity of avoiding lactonisation of the carboxylate salt to form the lactone enantiomers (VIIIa) or (VIIIb).

Figure 1:
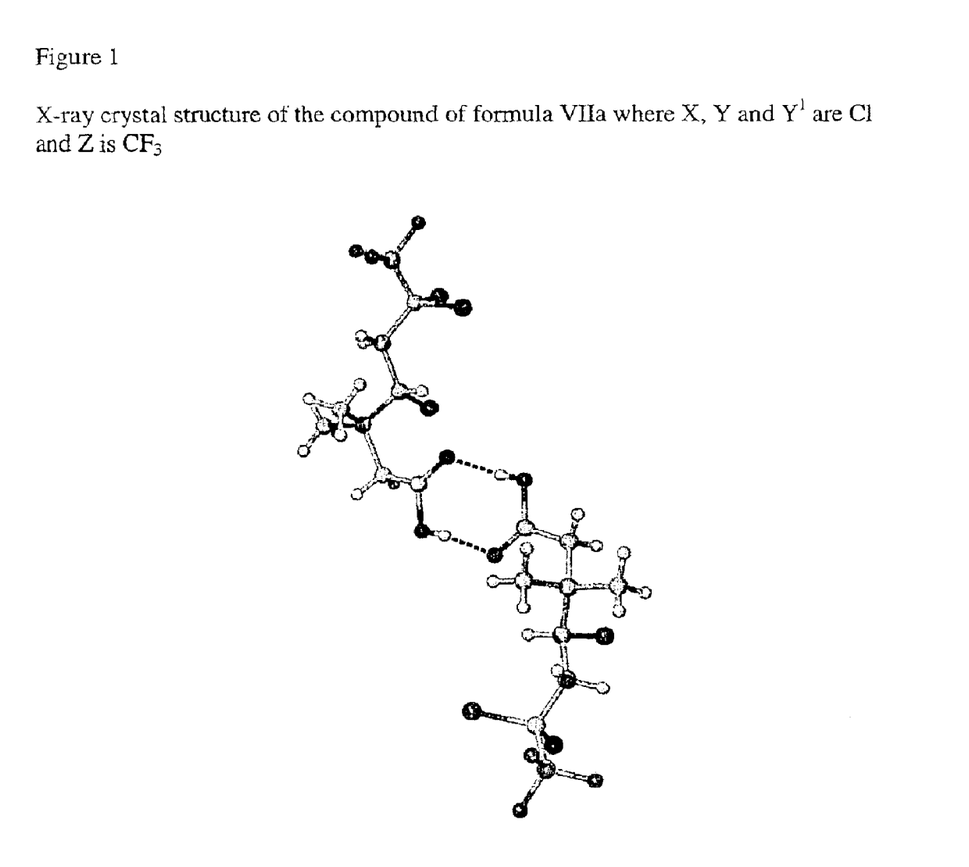

The applicants have devised a practical process for resolving compounds of formula (VII) into compounds (VIIa) and (VIIb)

wherein X is a leaving group; Y and $Y^1$ are independently Cl or Br; and Z is Cl, Br or a haloalkyl group without formation of appreciable amounts of the lactones (VIII). Both compounds of formula (VIIa) and (VIIb) may be used as the starting point for making active pyrethroid insecticides. The compounds with the most desired stereochemistry have been found to be the (−) enantiomers, which are compounds of formula (VIIa). The stereochemistry of the compound of formula VIIa where X, Y and $Y^1$ are Cl and Z is $CF_3$ has been confirmed by the applicants using X-ray crystallography (FIG. 1).

There is therefore provided a process for producing compounds of formula (VIIa) and (VIIb)

wherein X is a leaving group; Y and $Y^1$ are independently Cl or Br; and Z is Cl, Br or a haloalkyl group which process comprises:

a) reacting a compound of formula (VII)

wherein X, Y, $Y^1$ and Z are as defined for compounds (VIIa) and (VIIb) with a substantially optically pure chiral amine in a solvent to form a diastereoisomeric salt;

b) separating the diastereomeric salt of each enantiomer; and c) converting the diastereomeric salt of each enantiomer separately to compounds of formulae (VIIa) and (VIIb) by acid or base hydrolysis.

Further purification of the enantiomers may be undertaken if necessary or desirable.

A preferred leaving group X is Cl or Br.

Preferably Y and $Y^1$ are Cl.

Z is preferably Br, Cl or $CF_3$, especially Cl or $CF_3$ and most preferably $CF_3$.

The separation process of step b) may be achieved by any conventional means, for example fractional crystallisation or chromatography. In a preferred process, separation of the diastereomeric salts is achieved by selecting chiral amines that give diastereomeric salts with different solubility characteristics. As a result, the two diastereomeric salts can be forced into separate solvent systems, one of the enantiomeric salts being left in the mother liquors of the reaction mass while the other is removed.

In the context of this specification each alkyl moiety is a $C_1$–$C_6$ straight or branched chain and is, for example, methyl, ethyl, n-propyl, n-butyl, n-pentyl, n-hexyl, isopropyl, n-butyl, sec-butyl, iso-butyl, tert-butyl or neo-pentyl. Preferred alkyl groups are methyl and ethyl.

Halogen is fluorine, chlorine, bromine or iodine.

Haloalkyl groups are alkyl groups which are substituted with one or more of the same or different halogen atoms and are, for example, $CF_3$, $CF_2Cl$, $CF_3CH_2$ or $CHF_2CH_2$ and an especially preferred group is $CF_3$.

Suitable amines for use in the process are R(+)-alpha methyl benzylamine and (1S,2R)-1-amino-2-indanol and the preferred amine is R(+)-alpha methyl benzylamine. The preferred molar ratio of amine to acid (VII) is 0.4–0.6, most preferably 0.5–0.55.

Suitable solvents for step a) in the process are water/methanol, aprotic solvents such as toluene and esters such as ethyl acetate or isopropyl acetate.

Preferred solvents are aprotic solvents and in particular esters such as isopropyl acetate.

The process of step a) is performed at between 0–80° C., preferably at 25–65° C.

The process of step c) may be carried out using acid or base to dissociate the diastereoisomeric salts, but is preferably carried out with acid using mineral acid such as hydrochloric acid.

Isolation of the free acid can be by filtration or extraction into a solvent which may be an haloalkane such as dichloromethane, an aprotic solvent such as toluene, an aliphatic such as hexane or an ester such as isopropyl acetate. The process of step c) is performed at 0–50° C., preferably at 20–30° C.

If further purification of the resolved acids is required this may be done by standard methods such as recrystallisation. Suitable solvents include aliphatics such as hexane, isohexane or petroleum ethers or aromatic solvents such as toluene. Most preferably the solvent is hexane or isohexane.

The purification is performed at 0–100° C., depending upon the solvent of choice, preferably at 20–30° C.

The applicants have also succeeded in converting the (−)-enantiomer a compound of formula (VII) to the (+) cis forms of the compounds of the formula (III), (the stereochemistry required for making compounds with the highest insecticidal activity) demonstrating that the stereochemistry obtained by the process of the invention was preserved in subsequent reactions. It is already known that the (+) cis forms of compounds of the formula (III) are in fact the 1R cis enantiomers of formula (IIIa)

(IIIa)

which are ultimately convertible into desirable pyrethroid products of formula Ia with the 1R stereochemistry (Ia)

where Y and Z are as defined for formula (VII) above and E is an insecticidally active ester moiety such as those derived from 4-alkyltetrafluorobenzyl alcohols (especially 4-methyltetrafluorobenzyl alcohol), 4-alkoxytetrafluorobenzyl alcohols, α-cyano-3-phenoxybenzyl alcohol, 3-phenoxybenzyl alcohol and 2-methyl-3-phenylbenzyl alcohol (D Arlt et al, Ang, Chem. Int. Ed. Engl. 20, 703, (1981)).

Therefore in a further aspect of the invention there is provided a process for the preparation of a single enantiomer or enantiomerically enriched compound of formula (VI) wherein X is a leaving group such as Cl or Br; Y and $Y^1$ are independently Cl or Br and Z is Cl, Br or a haloalkyl group by the chlorination of a single enantiomer or enantiomerically enriched compound of formula (VII).

In yet a further aspect of the invention there is provided a process for the preparation of a single enantiomer or enantiomerically enriched compound of formula (V) wherein X is a leaving group such as Cl or Br; Y and $Y^1$ are independently Cl or Br; Z is Cl, Br or a haloalkyl group and R is an alkyl group by the esterification of a single enantiomer or enantiomerically enriched compound of formula (VI)

In a further aspect of the invention there is provided a process for the preparation of a single enantiomer or enantiomerically enriched compound of formula (IV) wherein Y and $Y^1$ are independently Cl or Br; Z is Cl, Br or a haloalkyl group and R is an alkyl group by the cyclisation of a single enantiomer or enantiomerically enriched compound of formula (V).

In yet a further aspect of the invention there is provided a process for the preparation of a single enantiomer or enantiomerically enriched compound of formula (III) wherein Y is Cl or Br and Z is Cl, Br or a haloalkyl group by the hydrolysis and dehydrochlorination of a single enantiomer or enantiomerically enriched compound of formula (IV).

In a further aspect of the invention there is provided a process for the preparation of a single enantiomer or enantiomerically enriched compound of formula (II) wherein Y is Cl or Br; and Z is Cl, Br or a haloalkyl group by the chlorination of a single enantiomer or enantiomerically enriched compound of formula (III).

In yet a further aspect of the invention there is provided a process for the preparation of a single enantiomer or enantiomerically enriched compound of formula (I) wherein Y is Cl or Br and Z is Cl, Br or a haloalkyl group and E is an insecticidally active ester moiety by the esterification of a single enantiomer or enantiomerically enriched compound of formula (II).

The individual steps of converting a compound of formula VII to a compound of formula I are known in the art or will be readily available to the skilled person. Thus compounds of formula VII or their enantiomers may be converted to compounds of formula VI or their enantiomers by reaction with a chlorinating agent and then esterified to a compound of formula (V) as described in 'March $4^{th}$ Edition—p437–38 and p392' respectively.

The (−) enantiomer of compound of formula (V) can be converted to give the required (+) enantiomer of formula (IVa), for example using the conditions given in EP-A-51355 or EP-A-3683. The other enantiomer of formula

(IVb) can be prepared in a similar manner from the (+) enantiomer of (V).

(IVa)

(IVb)

1R cis Compounds of formula (IIIa) (the + enantiomer) may be prepared by dehydrochlorinating and hydrolysing a compound of the formula (IVa) (the + enantiomer) by standard techniques, for example as described in U.S. Pat. No 4,238,505, to give compound of formula (IIIa). The compound of formula (IVb) can be converted in a similar manner to a compound of formula (IIIb).

(IIIa)

(IIIb)

The 1R (+) enantiomer of formula (IIIa) can be converted to the 1R cis acid chloride compound of formula (IIa) by standard techniques as in 'March 4$^{th}$ Edition—p437–38'. Similarly compounds of formula IIIb may be converted by the same processes to compounds of formula IIb.

(IIa)

(IIb)

The 1R compounds of formula Ia may be prepared by the reaction of a compound of formula (IIa) with an appropriate alcohol for example as given in EP-A-31199.

The (−) enantiomers and (+) enantiomers of compounds of formula (VII), (VI) (V) and certain compounds of formula (IV) are novel and as such form a further aspect of the invention.

Preferably the enantiomers of compounds of formula (VII), (VI), (V) and (IV) have an enantiomeric excess greater than 90%, more preferably greater than 98%.

The term "enantiomeric excess" is defined as:

$$\frac{(\%\ \text{major enantiomer}) - (\%\ \text{minor enantiomer})}{(\%\ \text{major enantiomer}) + (\%\ \text{minor enantiomer})}$$

Certain compounds of formula (I) are also novel and form yet another aspect of the invention.

The compounds of formula (I) can be used to combat and control infestations of insect pests such as Lepidoptera, Diptera, Hemiptera, Thysanoptera, Orthoptera, Dictyoptera, Coleoptera, Siphonaptera, Hymenoptera and Isoptera and also other invertebrate pests, for example, acarine, nematode and mollusc pests. Insects, acarines, nematodes and molluscs are hereinafter collectively referred to as pests. The pests which may be combated and controlled by the use of the invention compounds include those pests associated with agriculture (which term includes the growing of crops for food and fibre products), horticulture and animal husbandry, companion animals, forestry and the storage of products of vegetable origin (such as fruit, grain and timber); those pests associated with the damage of man-made structures and the transmission of diseases of man and animals; and also nuisance pests (such as flies).

Examples of pest species which may be controlled by the compounds of formula (I) include: *Myzus persicae* (aphid), *Aphis gossypii* (aphid), *Aphis fabae* (aphid), *Lygus* spp. (capsids), *Dysdercus* spp. (capsids), *Nilaparvata lugens* (planthopper), *Nephotettixc incticeps* (leafhopper), *Nezara* spp. (stinkbugs), *Euschistus* spp. (stinkbugs), *Leptocorisa* spp. (stinkbugs), *Frankliniella occidentalis* (thrip), *Thrips* spp. (thrips), *Leptinotarsa decemlineata* (Colorado potato beetle), *Anthonomus grandis* (boll weevil), *Aonidiella* spp. (scale insects), *Trialeurodes* spp. (white flies), *Bemisia tabaci* (white fly), *Ostrinia nubilalis* (European corn borer), *Spodoptera littoralis* (cotton leafworm), *Heliothis virescens* (tobacco budworm), *Helicoverpa armigera* (cotton bollworm), *Helicoverpa zea* (cotton bollworm), *Sylepta derogata* (cotton leaf roller), *Pieris brassicae* (white butterfly), *Plutella xylostella* (diamond back moth), *Agrotis* spp. (cutworms), *Chilo suppressalis* (rice stem borer), *Locusta migratoria* (locust), *Chortiocetes terminifera* (locust), *Diabrotica* spp. (rootworms), *Panonychus ulmi* (European red mite), *Panonychus citri* (citrus red mite), *Tetranychus urticae* (two-spotted spider mite), *Tetranychus cinnabarinus* (carmine spider mite), *Phyllocoptruta oleivora* (citrus rust mite), *Polyphagotarsonemus latus* (broad mite), *Brevipalpus* spp. (flat mites), *Boophilus microplus* (cattle tick), *Dermacentor variabilis* (American dog tick), *Ctenocephalides felis* (cat flea), *Liriomyza* spp. (leafminer), *Musca domestica* (housefly), *Aedes aegypti* (mosquito), *Anopheles* spp. (mosquitoes), *Culex* spp. (mosquitoes), *Lucillia* spp. (blowflies), *Blattella germanica* (cockroach), *Periplaneta americana* (cockroach), *Blatta orientalis* (cockroach), termites of the Mastotermitidae (for example *Mastotermes* spp.), the Kalotemitidae (for example *Neotermes* spp.), the Rhinotermitidae (for example *Coptotermes formosanus, Reticulitermes flavipes, R. speratu, R. virginicus, R. hesperus,* and *R. santonensis*) and the Termitidae (for example *Globitermes sulphureus*), *Solenopsis geminata* (fire ant), *Monomorium pharaonis* (pharaoh's ant), *Damalinia* spp. and *Linognathus* spp. (biting and suckling lice), *Meloidogyne* spp. (root knot nematodes), *Globodera* spp. and *Heterodera* spp. (cyst nematodes), *Pratylenchus* spp. (lesion nematodes), *Rhodopholus* spp. (banana burrowing nematodes), *Tylenchulus* spp.(citrus nematodes), *Haemonchus contortus* (barber pole worm), *Caenorhabditis elegans* (vinegar eelworm), *Trichostrongylus* spp. (gastro intestinal nematodes) and *Deroceras reticulatum* (slug).

The invention therefore provides a method of combating and controlling insects, acarines, nematodes or molluscs which comprises applying an insecticidally, acaricidally, nematicidally or molluscicidally effective amount of a novel compound of formula (I), or a composition containing a novel compound of formula (I), to a pest, a locus of pest, or to a plant susceptible to attack by a pest. The compounds of formula (I) are preferably used against insects, acarines or nematodes.

In order to apply a compound of formula (I) to a pest, a locus of pest, or to a plant susceptible to attack by a pest, a compound of formula (I) is usually formulated into a composition which includes, in addition to the compound of formula (I), a suitable inert diluent or carrier and, optionally, a surface active agent (SFA). SFAs are chemicals which are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of pests such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides an insecticidal, acaricidal, nematicidal or molluscicidal composition comprising an insecticidally, acaricidally, nematicidally or molluscicidally effective amount of a novel compound of formula (I) and a suitable carrier or diluent therefor. The composition is preferably an insecticidal, acaricidal or nematicidal composition.

In a still further aspect the invention provides a method of combating and controlling pests at a locus which comprises treating the pests or the locus of the pests with an insecticidally, acaricidally, nematicidally or molluscicidally effective amount of a composition comprising a novel compound of formula (I). The compounds of formula (I) are preferably used against insects, acarines or nematodes.

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$–$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at room temperature, it may be melted at a reasonable temperature, typically below 70° C.) or in solution (by dissolving it in an appropriate solvent)

and then emulsifiying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier).

Wetting agents, dispersing agents and emulsifying agents may be surface SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying pesticidal compounds. For example, it may be applied, formulated or unformulated, to the pests or to a locus of the pests (such as a habitat of the pests, or a growing plant liable to infestation by the pests) or to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a novel compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of suitable pesticides include the following:

a) Pyrethroids, such as permethrin, cypermethrin, fenvalerate, esfenvalerate, deltamethrin, cyhalothrin (in particular lambda-cyhalothrin), bifenthrin, fenpropathrin, cyfluthrin, tefluthrin, fish safe pyrethroids (for example ethofenprox), natural pyrethrin, tetramethrin, s-bioallethrin, fenfluthrin, prallethrin or 5-benzyl-3-furylmethyl-E-(1R,3S)-2,2-dimethyl-3 - (2-oxothiolan-3-ylidenemethyl)cyclopropane carboxylate;
b) Organophosphates, such as, profenofos, sulprofos, acephate, methyl parathion, azinphos-methyl, demeton-s-methyl, heptenophos, thiometon, fenamiphos, monocrotophos, profenofos, triazophos, methamidophos, dimethoate, phosphamidon, malathion, chlorpyrifos, phosalone, terbufos, fensulfothion, fonofos, phorate, phoxim, pirimiphos-methyl, pirimiphos-ethyl, fenitrothion, fosthiazate or diazinon;
c) Carbamates (including aryl carbamates), such as pirimicarb, triazamate, cloethocarb, carbofuran, furathiocarb, ethiofencarb, aldicarb, thiofurox, carbosulfan, bendiocarb, fenobucarb, propoxur, methomyl or oxamyl;
d) Benzoyl ureas, such as diflubenzuron, triflumuron, hexaflumuron, flufenoxuron or chlorfluazuron;
e) Organic tin compounds, such as cyhexatin, fenbutatin oxide or azocyclotin;
f) Pyrazoles, such as tebufenpyrad and fenpyroximate;
g) Macrolides, such as avermectins or milbemycins, for example abamectin, emamectin benzoate, ivermectin, milbemycin, spinosad or azadirachtin;
h) Hormones or pheromones;
i) Organochlorine compounds such as endosulfan, benzene hexachloride, DDT, chlordane or dieldrin;
j) Amidines, such as chlordimeform or amitraz;
k) Fumigant agents, such as chloropicrin, dichloropropane, methyl bromide or metam;
l) Chloronicotinyl compounds such as imidacloprid, thiacloprid, acetamiprid, nitenpyram or thiamethoxam;
m) Diacylhydrazines, such as tebufenozide, chromafenozide or methoxyfenozide;
n) Diphenyl ethers, such as diofenolan or pyriproxifen;
o) Indoxacarb;
p) Chlorfenapyr; or
q) Pymetrozine.

In addition to the major chemical classes of pesticide listed above, other pesticides having particular targets may be employed in the composition, if appropriate for the intended utility of the composition. For instance, selective insecticides for particular crops, for example stemborer specific insecticides (such as cartap) or hopper specific insecticides (such as buprofezin) for use in rice may be employed. Alternatively insecticides or acaricides specific for particular insect species/stages may also be included in the compositions (for example acaricidal ovo-larvicides, such as clofentezine, flubenzimine, hexythiazox or tetradifon; acaricidal motilicides, such as dicofol or propargite; acaricides, such as bromopropylate or chlorobenzilate; or growth regulators, such as hydramethylnon, cyromazine, methoprene, chlorfluazuron or diflubenzuron).

Examples of suitable synergists for use in the compositions include piperonyl butoxide, sesamex, safroxan and dodecyl imidazole.

Suitable herbicides and plant-growth regulators for inclusion in the compositions will depend upon the intended target and the effect required.

An example of a rice selective herbicide which may be included is propanil. An example of a plant growth regulator for use in cotton is PIX™.

Some mixtures may comprise active ingredients which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The following examples illustrate the processes and the compounds of this invention.

Chiral GLC Method for Analysis of Enantiomers

The following GLC method was used to analyse compounds of the formula (VII)

Column Chiraldex CB 25 m, 0.25 mm, 25 micron

Carrier gas helium

80° C. start temp. for 5 minutes, 2° C./min ramp rate to 120° C., 10° C./min ramp rate to 160° C., final time 2 minutes, total time 31 mins Injector temp 250° C.

Detector temp 250° C.

It was established that the enantiomer of (VII) ($Y, Y^1$ and X=Cl, Z=$CF_3$) with a (−) rotation eluted at 20.5 min. and that with a (+) rotation eluted at 21.3 min.

EXAMPLE 1

Preparation of the (−) enantiomer of 4,6,6-trichloro-7,7,7-trifluoro-3,3-dimethylheptanoic acid

Step A

Isopropyl acetate (400 ml) and 4,6,6-trichloro-7,7,7-trifluoro-3,3-dimethylheptanoic acid (54 gm) were charged to a clean, dry 1 liter jacketed reaction flask fitted with turbine agitator. The contents of the reactor were agitated at room temperature and R-(+)-α-methyl benzylamine (12.4 gm) was added slowly over 30 minutes producing a small exotherm. The reactor contents were then stirred for 2 days at room temperature after which time a fine white dispersion was obtained. The salt was filtered off on a sintered nutche and washed with a minimal ethyl acetate (~20 ml) followed by hexane (50 ml) and the white product pulled 'dry' on the nutche. Yield 17.7. gm.

Step B

The diastereomeric salt produced in step A was discharged into a 250 ml conical flask together with dichloromethane (50 ml). The flask contents were stirred on a magnetic stirrer whilst 2molar hydrochloric acid was charged (50 ml) and stirred to dissolve up the solids. The flask contents were then separated in a separating flask and the organic layer washed with further (50 ml) 2molar hydrochloric acid, followed by a water wash (50 ml) and a brine wash (25 ml). The organic layer was then topped to give a crystalline white solid (12.5 gm, 46%). Chiral GC analysis of the product revealed it to be 85% e.e. The crude product was recrystallised by dissolving in hexane (175 ml) and heating to 50° C. with agitation. The resultant colourless solution was then cooled in the fridge (+4° C.) to produce a small amount of white crystalline solid which was filtered off (2.52 gm) and found to be a mixture of the two enantiomers, 60% e.e. by chiral GC. The hexane filtrates were distilled to produce a white crystalline solid (9.2 gm), which was analysed by chiral GC as 92% e.e. of the required (−) enantiomer of 4,6,6-trichloro-7,7,7-trifluoro-3,3-dimethylheptanoic acid. Polarimetry on the enantiomer obtained in dichloromethane (12.34 g/liter) gave an $\alpha_D = -24°$ The stereochemistry of the compound was confirmed by X-ray crystallography under the conditions set out in Table 1. Atomic coordinates are set out in Table 2 and the X-ray crystal structure in shown in Figure I.

TABLE 1

| | |
|---|---|
| Empirical formula | C9 H12 Cl3 F3 O2 |
| Formula weight | 315.54 |
| Temperature | 293(2) K |
| Wavelength | 0.71073 Å |
| Crystal system | Triclinic |
| Space group | P1 |
| Unit cell dimensions | a = 6.4022(13) Å  α = 98.57(3)°. |
| | b = 8.8160(18) Å  β = 95.87(3)°. |
| | c = 12.393(3) Å  γ = 105.41(3)°. |
| Volume | 659.4(2) Å$^3$ |
| Z | 2 |
| Density (calculated) | 1.589 Mg/m$^3$ |
| Absorption coefficient | 0.717 mm$^{-1}$ |
| F(000) | 320 |
| Crystal size | 0.2 × 0.1 × 0.08 mm$^3$ |
| Theta range for data collection | 1.68 to 24.99°. |
| Index ranges | −5 <= h <= 7, −10 <= k <= 10, −14 <= l <= 14 |
| Reflections collected | 2968 |
| Independent reflections | 2968 [R(int) = 0.0000] |
| Completeness to theta = 24.99° | 95.0% |
| Absorption correction | Scalepack |
| Refinement method | Full-matrix least-squares on F$^2$ |
| Data/restraints/parameters | 2968/15/312 |
| Goodness-of-fit on F$^2$ | 1.042 |
| Final R indices [I > 2sigma(I)] | R1 = 0.1114, wR2 = 0.2830 |
| R indices (all data) | R1 = 0.1668, wR2 = 0.3 179 |
| Absolute structure parameter | 0.0(3) |
| Extinction coefficient | 0.057(15) |
| Largest diff. peak and hole | 0.892 and −0.534 e.Å$^{-3}$ |

TABLE 2

Atomic coordinates (×10$^4$) and equivalent isotropic displacement parameters (Å$^2$ × 10$^3$). U(eq) is defined as one third of the trace of the orthogonalized U$^{ij}$ tensor.

| | x | y | z | U(eq) |
|---|---|---|---|---|
| C(4A) | 710(40) | −5490(30) | −4096(19) | 55(6) |
| C(5B) | −4400(40) | 830(30) | 1912(18) | 54(6) |
| C(5A) | −820(30) | −5800(20) | −2343(17) | 50(6) |
| C(8B) | −1800(30) | 5640(30) | 1390(20) | 62(7) |
| C(7B) | −3580(30) | 4210(20) | 1560(17) | 44(5) |
| C(3A) | −1090(30) | −5300(20) | −3452(17) | 39(5) |
| F(3A) | −4090(30) | −11180(20) | −4085(14) | 97(5) |
| C(2B) | −6910(30) | −160(30) | 50(20) | 58(7) |
| C(8A) | −5810(30) | −9270(30) | −4515(18) | 46(5) |
| C(1B) | −5500(30) | −770(20) | −552(15) | 32(4) |
| C(4B) | −7890(40) | 1670(30) | 1540(20) | 62(7) |
| C(1A) | −2270(40) | −2810(20) | −2502(16) | 42(5) |
| C(9A) | −5550(40) | −10950(30) | −4850(20) | 62(7) |
| C(2A) | −870(30) | −35 10(30) | −3222(15) | 39(5) |
| C(6A) | −3440(40) | −6280(20) | −4110(18) | 52(6) |
| C(6B) | −4560(40) | 2750(30) | 652(18) | 58(6) |
| O(1A) | −4000(20) | −3571(18) | −2346(11) | 52(4) |
| F(1B) | 320(20) | 5712(18) | 3074(10) | 85(5) |
| O(2A) | −1230(20) | −1285(18) | −2002(11) | 54(4) |
| O(1B) | −6510(20) | −2279(17) | −1110(11) | 54(4) |
| O(2B) | −3600(20) | −120(16) | −634(11) | 51(4) |
| F(3B) | 1020(20) | 7841(15) | 2372(9) | 65(4) |
| F(1A) | −7460(20) | −12116(15) | −4925(11) | 68(4) |
| F(2B) | −1860(30) | 7152(18) | 3102(13) | 87(5) |
| F(2A) | −4830(30) | −11113(15) | −5805(11) | 58(3) |
| Cl(3B) | −2742(10) | 6989(7) | 676(6) | 76(2) |
| Cl(2A) | −6736(10) | −9110(7) | −3215(5) | 68(2) |
| Cl(1B) | −6141(9) | 3334(7) | −490(5) | 57(2) |
| Cl(1A) | −4111(9) | −5437(7) | −5300(4) | 54(2) |
| Cl(3A) | −7779(8) | −9032(7) | −5528(5) | 58(2) |
| Cl(2B) | 131(8) | 4973(7) | 660(5) | 57(2) |
| C(9B) | −600(40) | 6560(30) | 2440(20) | 57(6) |
| C(3B) | −6000(30) | 1320(20) | 1007(15) | 38(5) |
| C(7A) | −3530(30) | −7980(20) | −4433(19) | 48(5) |

EXAMPLE 2

Recovery of R-(+)-α-methyl benzylamine

The isopropyl acetate mother liquor and ethyl acetate washes, from the chiral diastereomeric salt formation of Example 1, were combined and washed with 2molar hydrochloric acid (2×50 ml), water (50 ml) and brine (25 ml). All separated well and were combined. The resultant aqueous liquor was washed with DCM (50 ml) then adjusted to pH>9 with 47% sodium hydroxide solution before extracting with DCM (100 ml). Topping off the resultant organic layer yielded a brown oil which represented a 95% recovery of R-(+)-α-methyl benzylamine.

EXAMPLE 3

Preparation of the (+) enantiomer of 4,6,6-trichloro-7,7,7-trifluoro-3,3-dimethylheptanoic acid The combined isopropyl acetate mother liquor/ethyl acetate washes from Example 1, after acid washing, was topped to yield a straw coloured solid (41.7 gm), which proved, by chiral GC, to be 32% e.e. compound of the (+) enantiomer of 4,6,6-trichloro-7,7,7-trifluoro-3,3-dimethylheptanoic acid.

EXAMPLE 4

Preparation of the (−) enantiomer of 4,6,6-trichloro-7,7,7-trifluoro-3,3-dimethylheptanoic acid Step A 4,6,6-Trichloro-7,7,7-trifluoro-3,3-dimethylheptanoic acid (45.1 gm–0.143 moles) was dissolved in water (120 ml) and methanol (180 ml) in 1 liter jacketed reaction flask fitted with turbine agitator, condenser, nitrogen purge and thermometer. The reactor contents were agitated whilst sodium carbonate (10.38 gm–0.074 moles) was added to dissolve the acid and the pH adjusted to 7.4. The reactor contents were heated to 50° C. to ensure complete solution. R(+)-alpha methyl benzylamine (9.11 gm–0.074 moles) was agitated in a 500 ml conical flask fitted with magnetic stirrer together with water (250 ml). Hydrochloric acid (38 ml 2molar) was then slowly added to dissolve up the amine giving a final pH of 2.5. The pH of the solution was adjusted with a few drops of 47% sodium hydroxide solution to pH 6. A dropping funnel was fitted to the acid solution reactor and the amine solution charged to it. The amine solution was then run into the acid solution at 50° C. over a period of 2 hours. When the addition was complete the reaction mass was heated for a further 30 minutes before allowing the contents to self cool—the reactor contents were allowed to cool overnight with agitation and precipitated a white solid. The final slurry was filtered off on a sintered nutche and pulled dry. The paste was given a small water methanol wash (20 ml water plus 40 ml methanol) and pulled dry. Yield 39.3 gm. The paste was slurried with 2molar hydrochloric acid and dichloromethane (200 ml of each) and agitated to dissolve. The two phases were separated and the organic layer treated with a second acid wash (200 ml) in the same way before applying a water (200 ml) and brine (100 ml) wash. The organic layer was then separated and the solvent removed on a rotary evaporator at 50° C. to give a pale yellow oil which solidified on cooling. Yield 28.8 gm.

Step B

The solidified product from step A was dissolved in hexane (190 ml) with agitation at 50° C. and then cooled to cool to 4° C. over 3 hours. A heavy white crystalline solid was formed which was filtered off (12.8 gm) and pulled 'dry'. Chiral GLC revealed this crystalline material was close to a racemic mixture of 4,6,6-trichloro-7,7,7-trifluoro-3,3-dimethylheptanoic acid. The resultant hexane filtrates were then evaporated on a rotary evaporator at 50° C. to give a yellow oil which solidified to a waxy yellow solid (5.9 gm). This solid was purified by column chromatography in two columns—each 2.9 gm of crude enantiomer onto an 80 gm silica column with 3 liters of 50:50 dichloromethane-:hexane eluent. The combined product from the columns yielded a crystalline product (3.2 gm, 14% yield). DSC analysis of the enantiomer gave a melting point of 61° C. and a molar purity of 92.8%. Chiral GC showed the material to be 90% e.e. of the required (−) enantiomer of 4,6,6-trichloro-7,7,7-trifluoro-3,3-dimethylheptanoic acid.

EXAMPLE 5

Preparation of the (+) enantiomer of 4,6,6-trichloro-7,7,7-trifluoro-3,3-dimethylheptanoic acid Step A Toluene (500 ml) and 4,6,6-trichloro-7,7,7-trifluoro-3,3-dimethylheptanoic acid (80.1 gm) were charged to a clean/dry 1 liter jacketed reaction flask fitted with turbine agitator. The contents of the reactor were agitated at room temperature in an attempt to dissolve the acid but some acid still remained. (1R,2S)-1-Amino-2-indanol (16.2 gm) was charged and the mixture stirred further at room temperature slowly dissolving to form a pale yellow solution. The reactor contents were stirred overnight producing a thick slurry which was filtered off and washed with a little toluene followed by hexane and eventually pulled 'dry' on the nutche. Yield 30.9 gm.

Step B

The diastereomeric salt was slurried in dichloromethane (100 ml) and given 2molar hydrochloric acid washes (3×50 ml) and a brine wash (50 ml). The organic phase was then topped to yield a very pale yellow/off white crystalline solid (21.4 gm). Chiral GC showed the product to be 40% e.e. of the (+) enantiomer of 4,6,6-trichloro-7,7,7-trifluoro-3,3-dimethylheptanoic acid.

Step C

The isolated solid was dissolved in hexane (150 ml) at 50° C. and was then cooled to 4° C. for 4 hours yielding a white crystalline solid, which was filtered off (11.5 gm). The hexane mother liquor was then topped to yield a pale yellow oil which solidified on standing (8.8 gm). Chiral GC showed this solid to be 66% e.e.. of the (+) enantiomer 4,6,6-trichloro-7,7,7-trifluoro-3,3-dimethylheptanoic acid. Further crystallisation was carried out on the solid using hexane (50 ml) producing a white crystalline solid (4.6 gm). The resultant hexane mother liquor was then topped to give a pale yellow solid (4.3 gm). Chiral GC on these products showed them to be to be 60% e.e. and 74% e.e. respectively of the (+) enantiomer of 4,6,6-trichloro-7,7,7-trifluoro-3,3-dimethylheptanoic acid. The latter of the two was re-dissolved in hexane (50 ml) and treated in the same way to give a third crystalline solid (1.1 gm), and material from the topped hexane mother liquor (2.9 gm, 7% yield as SE). Chiral GC showed them to be to be 56% e.e. and 90% e.e. respectively of the (+) enantiomer. Polarimetry of the 90% e.e. product in dichloromethane at 20° C. (12.07 gm/liter) gave an $\alpha_D = +28°$

EXAMPLE 6

Preparation of the (−) methyl ester of 4,6,6-trichloro-7,7,7-trifluoro-3,3-dimethylheptanoic acid Step A 4,6,6-Trichloro-7,7,7-trifluoro-3,3-dimethylheptanoic acid (−) enantiomer (20.0–0.063 moles, of 80% e.e. as judged by chiral GLC) was charged to a clean, dry 100 ml 3 necked flask fitted with thermometer, condenser, nitrogen purge and magnetic stirrer. Toluene (65 ml) and triethylamine (2 drops) were charged and the reactor contents agitated whilst heating to 70° C. with an external oil bath. Thionyl chloride (9.12 ml, 14.9 gm–0.125 moles) was added to the reaction flask by syringe over 45 minutes. The reactor contents were then allowed to cool and stirred overnight.

The following day the reactor contents were topped on a rotary evaporator and dichloromethane (30 ml) charged. This was also topped on the rotary evaporator to remove residual thionyl chloride, sulphur dioxide and hydrogen chloride from the acid chloride reaction. A yellow/brown oil was obtained (21.3 gm) which was analysed by GLC, GCMS and NMR to confirm the material was the acid chloride of 4,6,6-trichloro-7,7,7-trifluoro-3,3-dimethylheptanoic acid.

Polarimetry of the acid chloride (6.24 gm/liter at 20° C.) in dichloromethane gave an $\alpha_D = -24.0°$.

Step B

The acid chloride obtained in step A (20.0 gm–0.063 mol) was run into dry methanol (30 ml) which was stirred in a clean dry 100 ml reaction flask fitted with thermometer, condenser, nitrogen purge and magnetic stirrer. The reactor contents were stirred for a further 50 hours before topping off the methanol on a rotary evaporator to yield a red/brown oil (19.13 gm) which was analysed by GLC, GCMS and NMR to confirm the material was the methyl ester of 4,6,6-trichloro-7,7,7-trifluoro-3,3-dimethylheptanoic acid. Polarimetry of the methyl ester in dichloromethane (12.25 gm/liter at 20° C.) gave an $\alpha_D$=–23°.

EXAMPLE 7

Preparation of the (–) methyl ester of 4,6,6-trichloro-7,7,7-trifluoro-3,3-dimethylheptanoic acid 4,6,6-Trichloro-7,7,7-trifluoro-3,3-dimethylheptanoic acid (–) enantiomer (1.39 gm–0.004 moles, of 90% e.e. as judged by chiral GLC) was charged to a clean, dry 25 ml 3 necked flask fitted with thermometer, condenser, nitrogen purge and magnetic stirrer. Toluene (5 ml) and triethylamine (2 drops) were charged and the reactor contents agitated whilst heating to 70° C. with an external oil bath. Thionyl chloride (1.04 gm–0.009 moles) was added to the reaction flask by syringe over 20 minutes. The reactor contents were then allowed to cool and stirred overnight. The following day the reactor contents were topped on a rotary evaporator and toluene (5 ml) charged. This was also topped on the rotary evaporator to remove residual thionyl chloride, sulphur dioxide and hydrogen chloride from the acid chloride reaction. A yellow/brown oil was obtained which immediately quenched into dry methanol (10 ml) with agitation in a clean dry 25 ml flask agitated by a magnetic stirrer for 15 hours. Analysis by GLC showed the reaction to be complete and the solvent was topped to leave a pale yellow oil. The oil was dissolved in dichloromethane and washed with 2molar hydrochloric acid twice, water then brine. After drying the product was topped to yield a pale yellow oil (0.99 gm).

EXAMPLE 8

Preparation of the (+) methyl ester of 4,6,6-trichloro-7,7,7-trifluoro-3,3-dimethylheptanoic acid Step A 4,6,6-Trichloro-7,7,7-trifluoro-3,3-dimethylheptanoic acid (+) enantiomer (9.13 gm–0.029 moles, of 80% e.e. as judged by chiral GLC) was charged to a clean dry 100 ml 3 necked flask fitted with thermometer, condenser, nitrogen purge and magnetic stirrer. Toluene (32 ml) and triethylamine (2 drops) were charged and the reactor contents agitated whilst heating to 70° C. with an external oil bath. Thionyl chloride (4.16 ml, 6.78 gm–0.057 moles) was added to the reaction flask by syringe over 45 minutes. The reactor contents were then allowed to cool and stirred overnight.

The following day the reactor contents were topped on a rotary evaporator and dichloromethane (30 ml) charged. This was also topped on the rotary evaporator to remove residual thionyl chloride, sulphur dioxide and hydrogen chloride from the acid chloride reaction. A yellow/brown oil was obtained (11.44 gm) which was analysed by GLC, GCMS and NMR to confirm the material was acid chloride of 4,6,6-trichloro-7,7,7-trifluoro-3,3-dimethylheptanoic acid.

Polarimetry of the acid chloride in dichloromethane (5.78 gm/liter at 20° C.) gave an $\alpha_D$=+26°.

Step B

The acid chloride obtained from step A (10.19 gm–0.03 mol) was then run into dry methanol (30 ml) which was stirred in a clean dry 100 ml reaction flask fitted with thermometer, condenser, nitrogen purge and magnetic stirrer. The reactor contents were stirred for a further 50 hours before topping off the methanol on a rotary evaporator to yield a red/brown oil (7.83 gm–0.0237 mol) which was analysed by GLC, GCMS and NMR to confirm the material was the methyl ester of 4,6,6-trichloro-7,7,7-trifluoro-3,3-dimethylheptanoic acid.

Polarimetry of the methyl ester in dichloromethane (18.17 gm/liter at 20° C.) gave an $\alpha_D$=+26.4°.

EXAMPLE 9

Preparation of the (+) enantiomer of cis methyl 3-(2,2-dichloro-3,3,3-trifluoropropyl)-2,2-dimethyl-cyclopropane carboxylate The (–) enantiomer of the methyl ester of 4,6,6-trichloro-7,7,7-trifluoro-3,3-dimethylheptanoic acid (14.43 gm) was cyclised with sodium t-butoxide base (6.3 gm 100%) in t-butanol/DMF solvent at <0° C. to produce methyl 3-(2,2-dichloro-3,3,3-trifluoropropyl)-2,2-dimethyl-cyclopropane carboxylate which was isolated by quenching with water and extracting into dichloromethane. After washing with water and brine the product was obtained as a yellow/orange oil (10.1 gm) by topping off the dichloromethane solvent. The product obtained was analysed by GLC, GCMS and NMR to confirm the material was consistent with that of methyl 3-(2,2-dichloro-3,3,3-trifluoropropyl)-2,2-dimethyl-cyclopropane carboxylate and it had a 80/20 cis:trans ratio.

Polarimetry of the methyl 3-(2,2-dichloro-3,3,3-trifluoropropyl)-2,2-dimethyl-cyclopropane carboxylate in dichloromethane (5.84 gm/liter at 20° C.) gave an $\alpha_D$=+10.3°.

EXAMPLE 10

Preparation of (+) enantiomer of cis-Z 3-(2-chloro-3,3,3-trifluoro-1-propenyl)-2,2-dimethyl-cyclopropane carboxylic acid (+) Methyl 3-(2,2-dichloro-3,3,3-trifluoropropyl)-2,2-dimethyl-cyclopropane carboxylate cyclopropanecarboxylic (9.1 gm) was dissolved in methanolic potassium hydroxide (3.44 gm @100%) and heated to 60° C. in a clean dry 25 ml flask fitted with condenser, thermometer, nitrogen purge and magnetic stirrer. Heat was applied from an external oil bath. After 1 hour on temperature sodium carbonate (1.59 gm) was charged followed by ethanol (10 ml) and the reaction temperature increased to 90° C. and held for 8 hours to complete as judged by GLC. The product was obtained by topping off the solvent from the reaction, adding water (50 ml) and concentrated hydrochloric acid to adjust the pH to <2, followed by dichloromethane (50 ml). After separation a second similar dichloromethane wash of the aqueous phase was applied, separated and combined with the first wash. The combined organic layer was washed with water, brine and then topped to give a yellow paste (5.83 gm). The product obtained was analysed by HPLC, GCMS and NMR to confirm the material was consistent with that of structure (IIIa). HPLC revealed that the product was a mixture of Cis and Trans isomers in the ratio of ~85:15 respectively.

Polarimetry of the air dried crude product cis-Z 3-(2-chloro-3,3,3-trifluoro-1-propenyl)-2,2-dimethylcyclopropane carboxylic acid in dichloromethane (5.89 gm/liter at 20° C.) gave an $\alpha_D$=+24.1°.

EXAMPLE 11

Purification of cis-Z (+) 3-(2-chloro-3,3,3-trifluoro-1-propenyl)-2,2-dimethyl-cyclopropane carboxylic acid The crude acid obtained from Example 10 was recrystallised to give a product that was 100% cis-Z isomer by HPLC product (3.19 gm). The product was analysed by GLC, GCMS, NMR to ensure it was consistent with the structure of cis-Z 3-(2-chloro-3,3,3-trifluoro-1-propenyl)-2,2-dimethyl-cyclopropane carboxylic acid. Polarimetry of the purified product in dichloromethane (6.312 gm/liter) gave an $\alpha_D=+46°$. The rotation of cis-Z 1R (+) 3-(2-chloro-3,3,3-trifluoro-1-propenyl)-2,2-dimethyl-cyclopropane carboxylic acid is given in the literature +48° (U.S. Pat. No. 4,780,252 and +47° (PCT patent application No WO97/03941).

EXAMPLE 12

Preparation of cis-Z (+) 3-(2-chloro-3,3,3-trifluoro-1-propenyl)-2,2-dimethyl-cyclopropane carboxylic acid chloride A 1 liter dry, clean jacketed split reaction vessel equipped with agitator, thermometer, condenser, nitrogen blanket and vent to a scrubber system was charged with toluene (450 ml) and agitated whilst cis-Z (+) 3-(2-chloro-3,3,3-trifluoro-1-propenyl)-2,2-dimethyl-cyclopropane carboxylic acid (89.4 gm=0.369 mol) was added followed by triethylamine (0.21 gm=2.1 mmol). The reaction mixture was then heated to 45° C., using oil circulation on the jacket, and thionyl chloride (62.0 gm=0.52 mol) was then charged over 105 minutes maintaining on temperature. The reaction mass was then agitated for 5 hours at 45° C. then tested by GLC for completion of reaction showing 2% residual acid. A further addition of thionyl chloride (4.4 gm=37 mmol) was then made and the reaction mass allowed to cool with stirring overnight. The following day, residual thionyl chloride, dissolved sulphur dioxide and hydrogen chloride gases were removed by distillation of about 320 ml toluene under vacuum. GC, GCMS and NMR analysis of the product were consistent with the structure of the acid chloride (IIIa). Yield, 175 gm of a 54% solution of the acid chloride in toluene, ~97% theory. $\alpha_D=+46°$

EXAMPLE 13

Preparation of the (+) enantiomer of tefluthrin (2,3,5,6-tetrafluoro-4-methylbenzyl-(Z)-(1RS)-cis-3-(2-chloro-3,3,3-trifluoroprop-1-enyl)-2,2-dimethylcyclopropanecarboxylate Step A A 100 ml 3-necked round bottom flask was equipped with a stirrer bar, thermometer, PTFE syringe needle, reflux condenser, N$_2$ sparge and was vented to a caustic scrubber. To the reactor was charged (+) 1R cis-Z 3-(2-chloro-3,3,3-trifluoro-1-propenyl)-2,2-dimethylcyclopropane carboxylic acid chloride ((IIIa) [20.76 g (ca.54% w/w toluene solution), 43 mmol], then the acid chloride solution was heated to 42° C. with agitation. 2,3,5,6-Tetrafluoro-4-methylbenzyl alcohol (7.2 g, 37 mmol) in toluene (14 ml) was added to the reactor over 3 hr (via. syringe pump). The reaction was agitated at 25–42° C. for 4 days, then additional charges of the alcohol were made (total 1.6 g, 8.2 mmol). The reaction was then heated to 95° C. for 7 hr before cooling to room temperature.

Step B

The reaction mass was distilled under vacuum (100° C./10 mbar) to remove toluene. The product was a mid-brown oil (15.0 g, 80% yield, and when taking into account samples removed for analysis, the yield was about 95% of the (+) enantiomer of tefluthrin (2,3,5,6-tetrafluoro-4-methylbenzyl-(Z)-(1RS)-cis-3-(2-chloro-3,3,3-trifluoroprop-1-enyl)-2,2-dimethylcyclopropanecarboxylate.

GC/MS: 225, 197, 177, 141, 127, 101, 91

1H NMR (CDCl3): δ1.3 (s, 6H, geminal CH3), 2.0 (d, 1H cyclopropane ring), 2.15 (d, 1H cyclopropane ring), 2.3 (s, 3H, ArCH3), 5.2 (d, 2H, ArCH2O), 6.9 (d, 1H, CF3ClC=CH) The optical rotation of the product was measured in dichloromethane at 20° C. (5.56 g/liter) giving an $\alpha_D=+17°$.

What is claimed is:

1. A process for producing compounds of formula (VIIa) and (VIIb)

wherein X is Cl or Br; Y and Y$^1$ are independently Cl or Br; and Z is Cl, Br or a haloalkyl group which process comprises a) reacting a compound of formula (VII)

wherein X, Y, Y$^1$ arid Z are as defined for compounds (VIIa) and (VIIb) with a substantially optically pure chiral amine selected from R(+)-alpha methyl benzylamine and (1S,2R)-1-amino-2-indanol in a solvent to form a diastereoisomeric salt;

b) separating the diastereomeric salt of each enantiomer;

c) converting the diastereomeric salt of each enantiomer separately to compounds of formulae (VIIa) and (VIIb) respectively by acid or base hydrolysis.

2. The process according to claim 1 wherein X is Cl.

3. The process according to claim 1 or claim 2 wherein Y and Y$^1$ are both Cl and Z is CF$_3$.

4. The process for preparing an enantiomer of a compound of formula (III)

or an enantiomerically enriched compound of formula (III) wherein Y and Z are as defined in relation to formula (VII) in claim 1 comprising a) preparing an enantiomer of a compound of formula VII or an enantiomerically enriched compound of formula VII according to claim 1;

b) converting the product from step a) to give a single enantiomer or enantiomerically enriched compound of formula (VI)

VI wherein X, Y, Y¹ and Z are as defined in relation to formula (VII) in claim 1 by chlorination;

c) esterifying the product of step b) to give a single enantiomer or enantiomerically enriched compound of formula (V)

V wherein X, Y, Y¹ and Z are as defined in relation to formula (VII) in claim 1 and R is alkyl;

d) cyclising the product of step c) to give a single enantiomer or enantiomerically enriched compound of formula (IV)

IV wherein Y, Y¹ and Z are as defined in relation to formula (VII) in claim 1 and R is alkyl; and e) converting the product of step d) to a single enantiomer or enantiomerically enriched compound of formula (III) by hydrolysis and dehydrochlorination.

5. A process for preparing an enantiomer of a compound of formula (I)

I or an enantiomerically enriched compound of formula (I) where Y is Cl or Br, Z is Cl, Br or a haloalkyl group and E is an insecticidally active ester moiety selected from 4-alkyltetrafluorobenzyl alcohols, 4-alkoxytetrafluorobenzyl alcohols, α-cyano-3-phenoxybenzyl alcohol, 3-phenoxybenzyl alcohol and 2-methyl-3-phenylbenzyl alcohol, which process comprises a) preparing an enantiomer of a compound of formula III or an enantiomerically enriched compound of formula III according to claim 4;

b) chlorinating the product of step a) to give a single enantiomer or enantiomerically enriched compound of formula (II)

II where Y and Z are as defined above in relation to formula I; and c) esterifying the product of step b) to give a single enantiomer or enantiomerically enriched compound of formula (I).

6. The process according to claim 5 wherein E is derived from 4-methyltetrafluorobenzyl alcohol, α-cyano-3-phenoxybenzyl alcohol, 3-phenoxybenzyl alcohol or 2-methyl-3-phanylbenzyl alcohol.

7. The (−) enantiomer of a compound of formula (VII), formula (VI) or formula (V) or salts thereof:

wherein R is H or alkyl and X is Cl or Br; Y and Y¹ are independently Cl or Br; and Z is Cl, Br or a haloalkyl group.

8. The (+) enantiomer of a compound of formula (VII), formula (VI) or formula (V) or salts thereof:

-continued

V wherein R is H or alkyl and X is Cl or Br; Y and $Y^1$ are independently Cl or Br; and Z is Cl, Br or a haloalkyl group.

9. The (−) cis or trans enantiomer of a compound of formula (IV) or salts thereof:

IV wherein R is H or alkyl and Y, $Y^1$ and Z are Cl or Br.

10. The (+) cis or trans enantiomer of a compound of formula (IV) or salts thereof:

IV wherein R is H or alkyl and Y, $Y^1$ and Z are Cl or Br.

11. The (+) enantiomer of 2,3,5,6-tetrafluoro-4-methylbenzyl-(Z)-(1R 3R)-cis-3-(2-chloro-3,3,3-trifluoroprop-1-enyl)-2,2-dimethylcyclo- propanecarboxylate.

12. An insecticidal acaricidal and nematicidal composition comprising an insecticidally, acaricidally or nematicidally effective amount of the (+) enantiomer of 2,3,5,6-tetrafluoro-4-methylbenzyl-(Z)-(1R 3R)-cis-3-(2-chloro-3,3,3-trifluoroprop-1-enyl)-2,2-dimethylcyclo-propanecarboxylate.

13. A method of combating and controlling acarine or nematode pests at a locus which comprises treating the pests or the locus of the pests with an effective amount of the (+) enantiomer of 2,3,5,6-tetrafluoro-4-methylbenzyl-(Z)-(1R 3R)-cis-3-(2-chloro-3,3,3-trifluoroprop-1-enyl)-2,2-dimethylcyclopropanecarboxylate.

* * * * *